US009439361B2

(12) United States Patent
Teasdale

(10) Patent No.: US 9,439,361 B2
(45) Date of Patent: Sep. 13, 2016

(54) ROBOTIC PLANTLET HANDLING SYSTEM

(75) Inventor: Robert Dixon Teasdale, Chapel Hill (AU)

(73) Assignee: Nuplant Pty Ltd, Toowong (AU)

( * ) Notice: Subject to any disclaimer, the term of this patent is extended or adjusted under 35 U.S.C. 154(b) by 255 days.

(21) Appl. No.: 14/124,957

(22) PCT Filed: Jun. 8, 2012

(86) PCT No.: PCT/AU2012/000676
§ 371 (c)(1),
(2), (4) Date: Mar. 26, 2014

(87) PCT Pub. No.: WO2012/167332
PCT Pub. Date: Dec. 13, 2012

(65) Prior Publication Data
US 2014/0196366 A1    Jul. 17, 2014

(30) Foreign Application Priority Data

Jun. 8, 2011    (AU) ................................ 2011902262

(51) Int. Cl.
| | | |
|---|---|---|
| *A01G 9/02* | (2006.01) | |
| *A01G 9/10* | (2006.01) | |
| *B25J 9/00* | (2006.01) | |
| *A01G 9/08* | (2006.01) | |

(52) U.S. Cl.
CPC ................ *A01G 9/02* (2013.01); *A01G 9/086* (2013.01); *A01G 9/10* (2013.01); *A01G 9/1006* (2013.01); *A01G 9/108* (2013.01); *B25J 9/00* (2013.01); *Y10S 901/02* (2013.01)

(58) Field of Classification Search
CPC ............................ A01G 9/086; A01G 9/108

USPC ........................................... 47/1.01 P, 1.01 R
See application file for complete search history.

(56) References Cited

U.S. PATENT DOCUMENTS

| | | | | |
|---|---|---|---|---|
| 5,557,881 A | * | 9/1996 | Bouldin | ............... A01C 11/025 |
| | | | | 111/105 |
| 5,842,306 A | * | 12/1998 | Onosaka | ............... A01G 9/086 |
| | | | | 47/1.01 R |

(Continued)

FOREIGN PATENT DOCUMENTS

| | | |
|---|---|---|
| NL | 2001120 C2 | 6/2009 |
| WO | 9319581 A1 | 10/1993 |

(Continued)

OTHER PUBLICATIONS

PCT, International Search Report issued in PCT Application No. PCT/AU2012/000676, dated Aug. 28, 2012 (4 pages).

(Continued)

*Primary Examiner* — Kristen C Hayes

(57) ABSTRACT

There is provided apparatus including: a workstation having an operator work portion, a material source portion, a material delivery portion and a robot arm. A housing is located at the material source portion and contains plantlet holders, the housing being closable by a lid mechanically and sealingly engaging a peripheral lip of the housing. An empty housing is located at the material delivery portion to receive the plantlet holders. A tool assembly on the robot arm includes a plantlet holder manipulator for movement of a plantlet holder between the material source portion, the operator work portion, and the material delivery portion; and an integral closure manipulator operable to engage a lid for removal from and attachment to the housing.

35 Claims, 8 Drawing Sheets

(56) References Cited

U.S. PATENT DOCUMENTS 5,911,631 A * 6/1999 Bouldin ............... A01C 11/025
111/105
6,688,037 B2 * 2/2004 Keller ................... A01C 7/042
414/737

FOREIGN PATENT DOCUMENTS

WO         0252922 A1     7/2002
WO     2011014933 A1     2/2011

OTHER PUBLICATIONS

PCT, Written Opinion of the International Searching Authorty issued in PCT Application No. PCT/AU2012/000676, dated Aug. 28, 2012 (3 pages).

EPO Search Report in application EP 12 796 642.2, pp. 1-9.
Supplementary European Search Report in application EP 12 796 642, pp. 1-2.

* cited by examiner

ROBOTIC PLANTLET HANDLING SYSTEM

FIELD OF THE INVENTION

This invention relates to a robotic plantlet handling system. This invention has particular but not exclusive application to a robotic plantlet handling system for handling tissue cultured plantlets, and for illustrative purposes the invention will be described with reference to this application.

BACKGROUND OF THE INVENTION

The reference to any prior art in this specification is not, and should not be taken as, an acknowledgement or any form of suggestion that the referenced prior art forms part of the common general knowledge in the relevant art.

Plant tissue culture involves growth of plants (including plantlets) under usually sterile conditions in nutrient medium in glass or plastic containers. Plantlets are typically grown in groups of up to 40 individual shoots per container. After a suitable period of growth, shoot pieces or small plantlets can be dissected from the plantlets to be placed in new medium so that these will form roots or shoot growth for ex vitro rooting, or other tissue growth and further grow. There are often more dissected pieces (shoot tips, nodal segments, or small plantlets) than in the original container. Moreover, the plantlets from which shoot pieces have been dissected will generally form new shoots that will grow and be suitable for dissection and planting. In these processes multiplication occurs.

In the transfer of propagated plant material between culture media or between growing environments, the transfer protocols must be selected to overcome the inherent weakness of plantlets in culture media. In WO 2009/021274 there is described a method including the steps of segregating plantlets from a tissue-culture propagation medium into a root-permeable container containing a phytocompatible supporting aqueous gel medium comprising a nutrient solution gelled with an effective amount of a hydrocolloid gel-forming material, acclimating the segregated plantlets in light and air until the roots extend to the bottom of the container, and planting out the acclimated plantlet in its container.

The described method provides advantages over the prior art of the time. However, the container requires support in a tube or the like that requires manual separation for planting out. Accordingly it would be desirable to provide a plantlet holder that can support the plantlet between culture steps or between the final stage of propagation and planting out directly in the container, and able to be handled mechanically.

International Application PCT/AU2010/001008 (WO 2011/014933) discloses a plantlet holder having a pair of apertures in one side disposed about a partition line, and a single large aperture in the opposite side again disposed symmetrically about the partition line. The base portions are also configured to close up forming a base aperture. Handling tabs in the assembled plantlet holder present single handling portions having opposed respective handling pegs, and are adapted to be gripped by a handling robot. The handling portion doubles as a means for positive orientation by engaging in use in the recess portion of the plantlet holder support.

An embodiment of the culture system includes a plantlet handling apparatus including a housing formed of a light-transmitting polypropylene, a plantlet holder support similarly moulded in polypropylene, a plurality of plantlet holders, and a closure assembly.

In the robotic handling of plantlets using the above described plantlet holders, the housing containing medium and plantlets is placed in a material source space in a robot workstation having a robotic arm and a second container or containers are located at a material delivery space in the workstation. The robotic arm is programmed to collect a plantlet holder or holders sequentially from the source container and/or a supply of holders, deliver the holder or holders to a worker for any one of several necessarily-manual tasks, and deliver the actioned holders to the container or containers in the delivery space. The robotic arm in terminated in a gripper assembly adapted to cooperate with the handling tabs. The handling tabs also cooperate with a handling stand to support the plantlet holder at the worker space of the workstation. A limitation of the robotic handling arrangement is the need to manually remove and refit the container lids.

SUMMARY OF THE INVENTION

In one aspect the present invention resides broadly in robotic plantlet handing apparatus including:
   a workstation having an operator work portion, a material source portion, a material delivery portion and a robot arm;
   at least one housing located at the material source portion and containing a plurality of plantlet holders each comprising an open-topped container having apertures open to nutrient medium in use and having a handling lug, the housing being closable by a lid having a complementary engagement periphery adapted to mechanically and sealingly engage a corresponding peripheral lip of the housing;
   at least one said housing located at said material delivery portion and adapted to receive a plurality of said plantlet holders;
   a plantlet holder manipulator on said robot arm and adapted to engage said handling lug for movement of a plantlet holder between said material source portion, said operator work portion, and said material delivery portion; and
   a closure manipulator on said robot arm and selectively operable to engage a said closure for removal from and attachment to the housing.

DESCRIPTION OF THE INVENTION

This application claims the priority of an earlier application AU2011902262. The applicant states under Rule 4.18 that any relevant material that is not otherwise contained in this application but is completely contained in the earlier application, that element or part is incorporated by reference in this application.

The workstation is generally a clean space where substantially sterile materials may be handled. For example the workstation may comprise a workstation enclosure such as positive pressure, laminar flow or glove box enclosure.

The operator work portion may include one or more work stands adapted to receive and retain a plantlet holder for a worker to operate on the plantlet in the holder. The work stands may include a handling lug engagement portion adapted to cooperate with a complementary engagement portion on the handling tab of the plantlet holder. The operator work portion may include lighting. The operator work portion may include robot operating controls and/or overrides. The operator work portion may include a plant tissue and nutrient waste and reject holder disposal means. The operator work portion may comprise a hinged platform mounting the work stands and movable to permit changing out of a waste and reject holder located beneath an opening in the platform. The hinge may be configured to release the platform at a selected angle.

The operator work portion may include a plurality of work stands each including operator prompt means adapted to cause the operator to time actions in concert with the robot arm. The operator prompt means may comprise one or more LED indicators operated by control means associated with the robot arm.

There may be provided latch means allowing the work stand to be selectively released from the operator work portion for maintenance, cleaning or replacement. The work stand may include retaining means selectively operable to retain and release a plantlet holder. For example, there may be provided a retaining means movable by a plantlet holder gripper against a bias from a position allowing insertion and removal of the plantlet holder and a position retaining an inserted plantlet holder in the work stand.

The material source portion may include an array of housings. The array of housings may include location means for the respective housings to assist the robot arm operation by location of the plantlet holders within tolerance of discrete positions. The material source portion may include a closure locator to allow for storage of a lid removed from a housing and/or spare closures. The material source portion may include storage for spare plantlet holders.

The material delivery portion may include space for an array of housings. The array of housings may include location means for the respective housings to assist the robot arm operation by providing discrete locations for the plantlet holders. The material source portion may include a lid locator to allow for storage of a lid to be fitted to a housing and/or spare lids.

The workstation may include other portions selected from but not limited to a hand tool storage portion and a tool sterilization bath portions.

The robot arm may comprise a multi-axis robot arm controlled by a robotic controller and terminating in the plantlet holder manipulator. The plantlet holder manipulator may comprise a gripper assembly having a pair of jaws adapted to engage the handling tab of the plantlet holder and selectively operable under robotic control by means such as electromechanical or pneumatically actuator. The jaws may have complementary profiles adapted to grip the plantlet holder lugs. The end portions of the gripper arms may be provided with a friction-modifying coating or sheathing to optimise plantlet holder handling.

The closure manipulator on the robot arm may take the form of a discrete tool and will be of a form dictated by the form of the interaction with the closure. The closure and housing may be formed of a resilient material. In this case the interaction may comprise a squeezing or other distortion of the closure resulting in the closure being dislodged from the housing to remove the closure. The resilience of the closure and/or housing material may be selected to be an inherent contributor to the sealing closure of the housing in use.

The closure manipulator may comprise a pair of arms having outer ends adapted to engage engagement portions on the closure whereby relative movement of the respective outer arm ends toward each other causes an installed closure to be released by distortion from the housing, the outer arm ends being further adapted to retain the removed closure. The robot arm may then move the closure to a closure storage location in the workstation. The outer arm ends may be configured to engage a free closure and install it on an open housing with the motive force of the robot arm.

The closure may include integrally formed recesses into which the outer ends may pass. The outer ends may include nibs or barbs adapted to engage a corresponding boundary part of the recesses. By this means the arms may be expanded to locate a lid closure for carriage without the need to grip. The outer ends may be stepped such that a shoulder may bear on the edges of the recess to permit the robot arm to press the lid closure on to the housing. The outer ends may be spread, when located in the recesses of a closure in situ on a housing, to distort the closure and underlying parts of the housing to disrupt the sealing engagement and allow lid removal.

The closure manipulator may be integrated with the gripper assembly forming the plantlet holder manipulator. For example the closure manipulator may share a common actuator with the gripper assembly. The gripper assembly function and closure manipulator function may be integrated into a gripper/closure manipulator assembly. For example, the gripper/closure manipulator may comprise a manipulator body mounted on the robot arm, a pair of arms each having a gripper portion disposed at one end of the arm and a closure manipulator portion disposed at the other end of the arm, the arms each being pivoted to the manipulator body between the gripper portion and a closure manipulator portion to form a gripper and a closure manipulator, and actuator means mounted on the manipulator body to work the arms in concert to operate said gripper and closure manipulator.

The gripper assembly, closure manipulator and/or gripper/closure manipulator may be mounted on the robot arm on a rotatable cuff to enable selective deployment of the grippers and closure manipulator by rotation of the cuff.

The actuators of the gripper assembly, closure manipulator or gripper/closure manipulator may be pneumatic or electromechanical. In any case a rotatable cuff may include means to control the spooling of control cables or tubes to enable rotations of more than +/−180°. For example the rotatable cuff may include two or more relatively rotatable cable drums whereby the connecting cable is wound from one drum to the other and back as the gripper and/or manipulator are rotated. The respective drums may be separated by a half-speed idler body having low-friction leads or rollers for the laying or playing out of the cables or tubes on or from the respective drums.

The housing may be formed of any material compatible for use in conjunction with plantlet raising conditions and media. For example the housing may comprise a polypropylene tub or tray. The housing is preferably transparent or translucent. For example the housing may be made of food grade polypropylene such as that used to produce take-away food containers. The housing may include integrally formed sealing means adapted to cooperate with the lid to provide the substantially airtight seal.

The housing may include an integral supporting portion adapted to cooperate with the plantlet holder support to maintain the plurality of plantlet holders in the nutrient medium in use. Alternatively the housing may include an integral plantlet holder portion. For example the housing may be formed with integral wells each configured to support a plantlet holder.

The housing may comprise a substantially flat bottomed enclosure for the nutrient medium and into which the supported plantlet holders depend. The void volume of nutrient medium between plantlet holders may be controlled by the use of integrally moulded void filler portions. Alternatively the housing base may be provided with re-entrants to enable close stacking of housings with the plantlet holder support and plantlet holders installed. For example the housing base may be formed with integral recesses adapted to cooperate with upper portions of the plantlet holders whereby the upper portions are located in the integral recesses in the stack.

The location means may take the form of housing holders located in a workstation/robot enclosure at the material source and delivery stations. The housing holders may take the form of an aperture plate having apertures for accepting a plurality of housings. The housing holder may include latching means to provide selectively releasable, positive retention of the housing in the housing holder. The housing may be formed with nibs formed in a side wall to cooperate with the latching means. Otherwise, the nibs may be configured to enable snap-in retention in the location means for the respective housings. The nibs may provide for handling stability, for example, when closures are being removed therefrom. The housing holder may be releasable from the workstation to change multiple housing in or out of a workstation enclosure.

The closure may comprise any suitable lid adapted to close off an open top of the housing by means of a substantially airtight seal. For example the closure may comprise a lid having a complementary engagement periphery adapted to mechanically and sealingly engage a corresponding peripheral lip of the housing. In the case of the polypropylene housings described above, the common and well developed technology in respect of sealing mechanical closure of take-away food containers may be utilized.

The maintenance of an isolated environment inside the housing by way of the mechanical seal between the housing and the closure is of course compromised by opening the housing. The closure may from time to time be opened. While the acclimation environment may be kept as clean as possible, contamination may occur. It has been surprisingly determined that contamination is reduced by providing the closure with a relatively deep peripheral flange that extends downward of the housing lip to define an annular dead space that is not subject to convection mixing with the environment. The flange appears to lower the risk of contamination by influencing the flow of condensation and airborne aerosols and particles entering the housing.

In a typical plantlet culture environment, a suitable flange may extend below the sealing rim of the housing sufficient to form an air gap which may avoid capillary entrapment of a water bridge across the seal. For example, the flange may extend at least 3 mm and preferably 8 to 10 mm). Preferably the annular space is narrow enough to achieve the desired convection mixing control but not so narrow as to form a surface tension trap for condensation. Where a deeper flange is preferred, there may be mechanical constraints such as the need to distort the flange by a sufficient degree to open the housing. In these cases the flange may be stepped whereby the selected narrow annular space is bounded at is lower edge by an outward step to a lower flange portion, whereby there is provided a lower annular space providing a degree of reduced convection mixing and of a width sufficient to permit removal of the closure from the housing and an upper annular space selected to substantially resist convection mixing.

The closure may have a peripheral flange that is spaced inwardly of and extends downward of the housing lip to define an annular drip line for condensation away from the lip. By this means the seal between the housing and closure does not attract and retain liquid condensate as a conduit for contamination.

The closure may have its selected permeability to metabolic gases produced or required by plantlets provided by inclusion of a gas permeable portion of the closure. Preferably the closure for said housing includes a gas permeable portion of either film material or fibrous material selected to allow exchange of metabolic gases produced or required by plantlets. The material may be hydrophobic or hydrophilic. For example, film materials may be selected from hydrophobic polyolefin materials. Fibrous materials may comprise hydrophilic or hydrophobic fibres in a woven or non-woven mat. There may be provided a cellulosic non-woven material having a proportion of polyolefin fibre therein to permit the mat to be heat sealed to a substrate such as the closure body.

Hydrophobic permeability of the closure to metabolic gases may be provided by any suitable means. By hydrophobic permeability to metabolic gases it is meant that metabolically relevant transfer of metabolic gases such as $CO_2$ and $O_2$ may relatively freely exchange through the closure. The material may be selected for its ability to control water vapour to tend water to be retained inside the housing. For example, there may be provided a closure including an annular body adapted to seal the housing closed and including a permeable closure portion closing over the aperture of the annulus and formed of a gas permeable hydrophobic material.

The gas permeable hydrophobic material may be selected from axially oriented crystalline polyolefins and other suitable membranous materials, and non-woven sheet materials. For example the hydrophobically permeable material may be selected from the synthetic materials, PP (Polypropylene), LDPE (low density polyethylene film), PVC (unplasticized polyvinylchloride film) and FEPC (fluorinated ethylene propylene copolymer film):

The gas permeable hydrophilic material may be selected from non-woven fibrous sheet materials, such as cellulose fibres with inclusion of a proportion of polyolefins to allow heat-sealing to the closure. The fibrous materials are selected to allow relatively free transfer of all gases, including water vapour, through the sheet material, but represent a tortuous path inhibiting the entry of particulate biological contaminants.

The permeable portion may be mechanically engaged with a body portion of the closure, or may be adhered to the closure body by adhesive or heat sealing. In the case of a moulded polymer closure, the closure may be formed with one or more apertures which are occluded by one or more layers of permeable material bonded or heat sealed to the inner or outer surface of the closure body. The permeable material may for example comprise biaxially oriented polypropylene (BOPP) which is able to be autoclaved for sterilization of the assembled closure while being heat sealable to a polypropylene closure body.

One example of a suitable hydrophobic and permeable material is biaxially oriented polypropylene (BOPP) laminate comprising film co-extruded on one or both sides with polyolefinic copolymers forming a heat sealable layer. Such films find applications based on the gas permeability properties, such as improving the shelf life of fresh produce and other applications requiring a high gas transfer rate. Typical values are an overall thickness of about 35 µm, yielding 31.4 $m^2$ $kg^{-1}$ and having permeabilities (24 hr) of 2.7 $Lm^{-2}$ ($O_2$) and 10.8 $Lm^{-2}$ ($CO_2$). Water vapour permeability varies from 0.8 gm$^{-2}$ per 24 hrs at 23° C. and 85% RH to 6.0 gm$^{-2}$ per 24 hrs at 38° C. and 90% RH.

The plantlet holders may have access apertures of form dictated by functions other than allowing the diffusion of nutrients and metabolites and the egress of roots. For example, the apertures may be shaped having a transverse opening larger at the upper end than at the lower end. In addition to or in lieu of an aperture, the side wall of the plantlet holder may be relieved downward of the upper edge to provide access for a scalpel to trim or excise new plantlets from the main plant, requiring access to the basal portion of the plantlets from below the agar surface. For example there may be provided a generally V-shaped notch or valley extending from the upper edge. The relieved portion may intersect an aperture in the side wall to provide a deeper re-entrant. The apertures may comprise one or more vertical slots.

The handling lug may comprise a projection providing means for handling the plant holder by manual or mechanical means. Complementary engagement portions on the handling lug of the plantlet holder may comprise a cross pin or laterally extending pair of pegs, wherein the handling lug engagement portion of the work stand comprises a pillar mounted to the work station and having a bifurcated top admitting a portion of the handling lug and a an upper transverse groove extending either side of the bifurcation of the top and adapted to receive the cross pin or pegs.

The plantlet holders may be formed in multiples as a stock moulding wherein complementary halves of the plantlet holder are formed either side of a joiner strip. A residual part of the joiner strip may include a self-hinge portion whereby the plantlet holder portions may be assembled by folding the parts relative to the closed plantlet holder.

Computer controlled mechanical handling means including the robotic controller may form part of an integrated plant handling apparatus including electronic control of subsystems including one or more of plantlet holder excision and assembly, sterilization of parts, mixing and dispensing of nutrient media, changeover of nutrient media, insertion of plantlets into the plantlet holder support, handling supported plantlet holders en mass or plantlet holders individually, or the like.

The plantlet holder support may take any suitable form. For example there may be provided a support system for a plurality of the above plantlet holders and including a moulded or sheet-formed body having a plurality of apertures into which the assembled plantlet holders are located, the apertures serving as engagement means maintaining the plantlet holders in assembly for handling en mass.

In a further aspect this invention resides broadly in a plant cloning method including the steps of:
(i) providing a workstation having an operator work portion, a material source portion, a material delivery portion and a robot arm;
(ii) locating in said workstation at least one housing at the material source portion and containing plantlets in a plurality of plantlet holders each comprising an open-topped container having apertures open to nutrient medium in use and having a handling lug, the housing being closed by a lid having a complementary engagement periphery adapted to mechanically and sealingly engage a corresponding peripheral lip of the housing;
(iii) locating in said workstation at least one housing at said material delivery portion and adapted to receive a plurality of said plantlet holders;
(iv) operating said robot arm and a closure manipulator thereon to engage and remove said lid and deliver the lid to a storage location;
(v) operating said robot arm and a plantlet holder manipulator thereon to engage the handling lug of and remove a plantlet holder from the housing at the material source portion and deliver the holder to a work stand adapted to receive and retain the plantlet holder for a worker to operate on the plantlet in the holder;
(vi) operating on the plant material to produce one or more product-containing plantlet holders;
(vii) operating said robot arm and a plantlet holder manipulator thereon to engage the handling lug of and remove a plantlet holder from a work stand to a said housing at said material delivery portion;
(viii) repeating step (vii) to exhaust product bearing plantlet holders on work stands;
(ix) repeating steps (v) to (viii) until a said housing at said material delivery portion is loaded; and
(x) operating said robot arm and said closure manipulator thereon to engage a lid and install the lid on said loaded housing.

The methods of the present invention are amenable to robotic implementation. For example there may be provided a robotic platform comprising a six-axis robot that operates in a sterile laminar flow cabinet with suitably high precision such as 0.02 mm repeatability and speed such as up to 4.4 m/s.

For use in a cloning mode, a batch of up to nine containers (for example 216 plantlet holders) may be loaded consisting of up to three sealed containers of input plantlets (ready for subculture) that are sprayed with alcohol (surface decontamination) as they are loaded into a tray that quickly snaps into the robotic platform. Up to six output containers with empty plantlet holders are similarly sprayed and inserted into trays; these are filled with agar-gelled medium. The container lids are robotically removed (using integrated grip points) to a storage area within the sterile cabinet.

In the basic cloning mode, the first two plantlet holders (with plantlets) from the first input container are, in sequence, gripped by the robotic fingers and transferred to two corresponding plantlet holder-stands where they are suspended in front of the operator, alongside two output plantlet holders similarly transferred from the first output container. The operator readily excises a shoot (or other tissue) from the first input plantlet and transfers this to the first output plantlet holder, and signals completion using foot or other controls.

The robot fingers grip the finished output plantlet holder and quickly returns this to an empty position in the output container, then return with a replacement plantlet holder. Similarly, when all available dissections have been made from the first input plantlet holder, the operator may signal this with foot or other controls, and it is removed to the input container, and replaced. The operator thereby may always have at least one input plantlet and one empty output plantlet holder available to continue working, with the robot removing and replacing these as signalled.

While a cycle time of about six seconds is short, the operator is not rushed but has only to make the key dissection in a very accessible position, and directly controls the timing.

There may be several other options within the cloning program. Different types of explants may grow differently, so that separation is desirable. For example, micro-cutting methods typically produce tips and nodes; tips will root more rapidly and grow vertically from the apex, whereas with nodes rooting is often delayed until an axillary shoot develops, which will be at an angle to the stem, and multiple shoots often form. The present system allows optional grading of input and output plants.

A graphic interface may report progress in plan view. For example, a screen image may be placed for dissection and may visually illustrate status. The system may also facilitate rapid grading without dissection, such as for quality control and consolidation before shipping. The cycle time for grading is typically under three seconds per plantlet. Image-processing for automatic grading may also be included.

One feature of the system is the ability to change medium, and this may be performed with minimal operator input. Input containers and corresponding receiving containers with the new (liquid) medium are loaded and positions designated and viewable in the screen image. Feedback on progress is also provided graphically. Transfer time may be approximately three seconds per plantlet, and operators can attend to other duties while a set of four pairs of containers are transferred. Speed and other variables are readily adjusted through a configuration page.

The robotic system also may provide data and image collection capability, allowing tracking of individual plantlets through all subcultures through to nursery transfer.

Such tracking may provide clients with data for further improvement of subculture and growth regimes. It may also provide a management tool to flag time and location for collection of plantlets for dissection or other transfers, and monitoring of operator performance for positive feedback.

BRIEF DESCRIPTION OF THE DRAWINGS

The invention will be described with reference to the following non-limiting embodiment of the invention as illustrated in the drawings and wherein:

In FIGS. 1 and 2 there is illustrated the workstation 10 with the laminar-flow cabinet substantially cut-away for clarity. A platform 11 mounts a multi-axis robotic arm 12 located within an array comprising a material source portion 13, an operator workstation portion 14 and a delivery portion 15. The robot arm mounts a tool assembly 16 (illustrated in FIG. 3) described in detail hereinafter.

Figure 1:
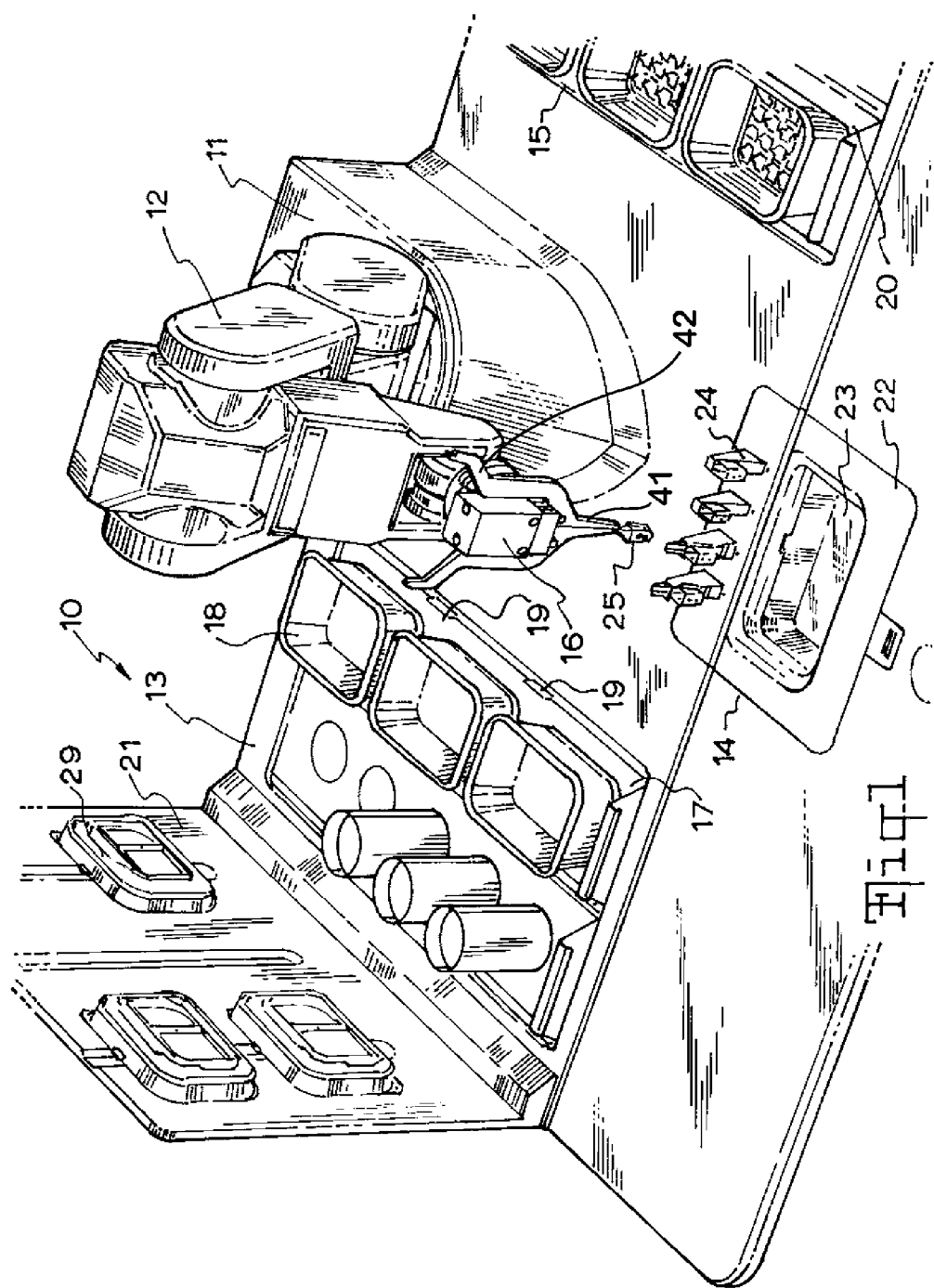
FIG. 1 is a perspective view of a robotic arrangement in accordance with the present invention.

The material source portion 12 includes a removable, apertured plate 17 having wells for locating plantlet handling containers 18. The delivery portion 15 has a removable, apertured plate 20 having wells for locating plantlet handling containers to be filled. Latch mechanisms 19 selectively retain the housings 18 in the respective plates 17, 20 by interaction with nibs formed in the housings 18. A lid storage plate 21 stores closure assemblies 29 for closing the housings 18 when filled.

The operator portion 14 comprises a hinged and removable plate 22 having a waste well including a disposable waste container 23. Four work stands 24 (illustrated in more detail in FIGS. 4 and 5) are adapted to receive plantlet holders 25 described in more detail hereinafter. The plate 22 has an LED indicator 28 corresponding work stand 24, the respective LED indicators 28 being collectively wired to a quick release connector (not shown) to permit removal of the plate 22.

Figure 2:
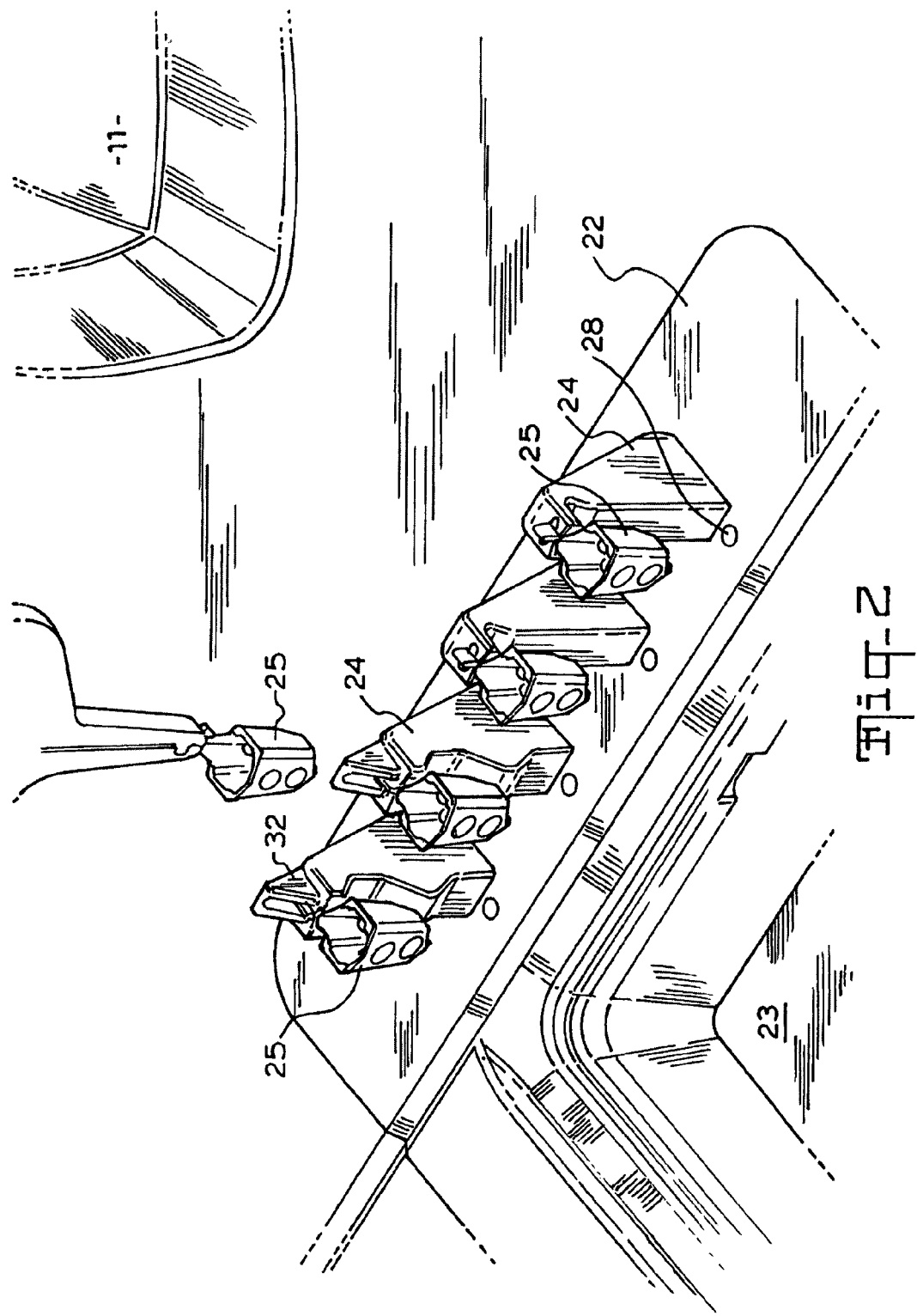
FIG. 2 is a detail view of the apparatus of FIG. 1 in use.
Figure 5:
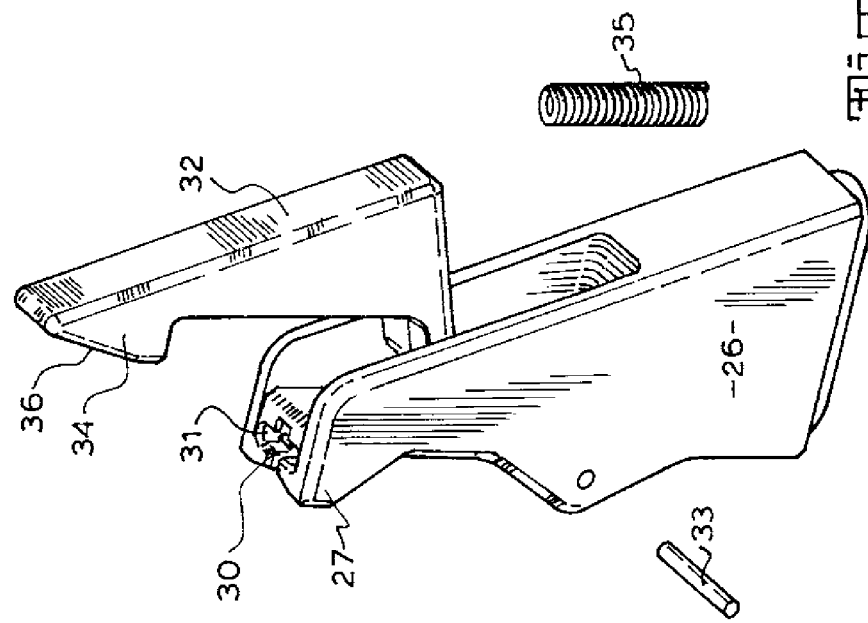
FIGS. 4 and 5 are views of a work stand adapted for use in the apparatus of the present invention, in assembly and exploded view respectively.
Figure 4:
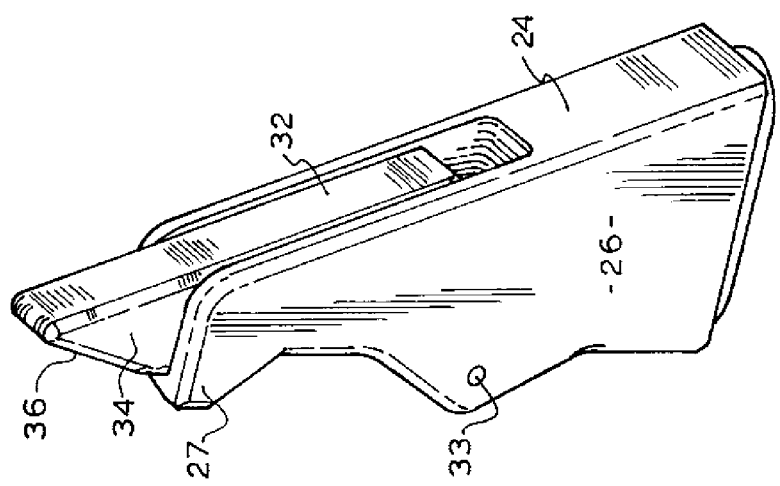

As illustrated in FIGS. 4 and 5, the work stand 24 includes a body 26 releasably secured to the plate 22 and having an overhanging upper portion 27. A slot 30 is adapted to receive a handling lug of a plantlet holder 25. A transverse groove 31 cooperates with a transverse peg arrangement on the handling lug of the plantlet holder 25 as described hereinafter. A plantlet holder may be securely retained for work in a work stand 24 by an optional latch 32. The latch 32 is pivoted to the body 26 by pivot pin 33. The latch 32 has a head portion 34 adapted to be urged over the upper portion 27 by the action of a spring 35. The head portion 34 also has a camming surface 36 against which a tool on the robot arm 12 may press to displace the latch 32 from the upper portion 27 to permit the plantlet holder to be inserted to and removed from the work stand 24. Installation of both latched and latchless work stands 24 is illustrated in FIG. 2.

Figure 3:
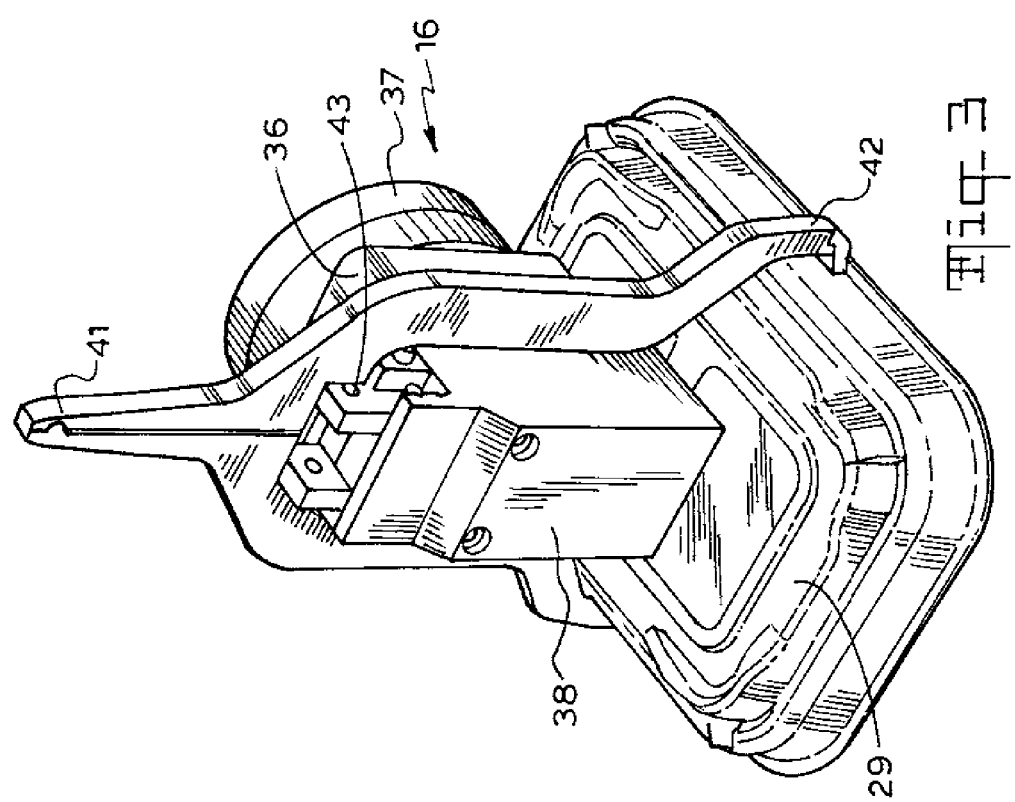
FIG. 3 is a detail view of a tool head for use with the apparatus of FIG. 1.
Figure 6:
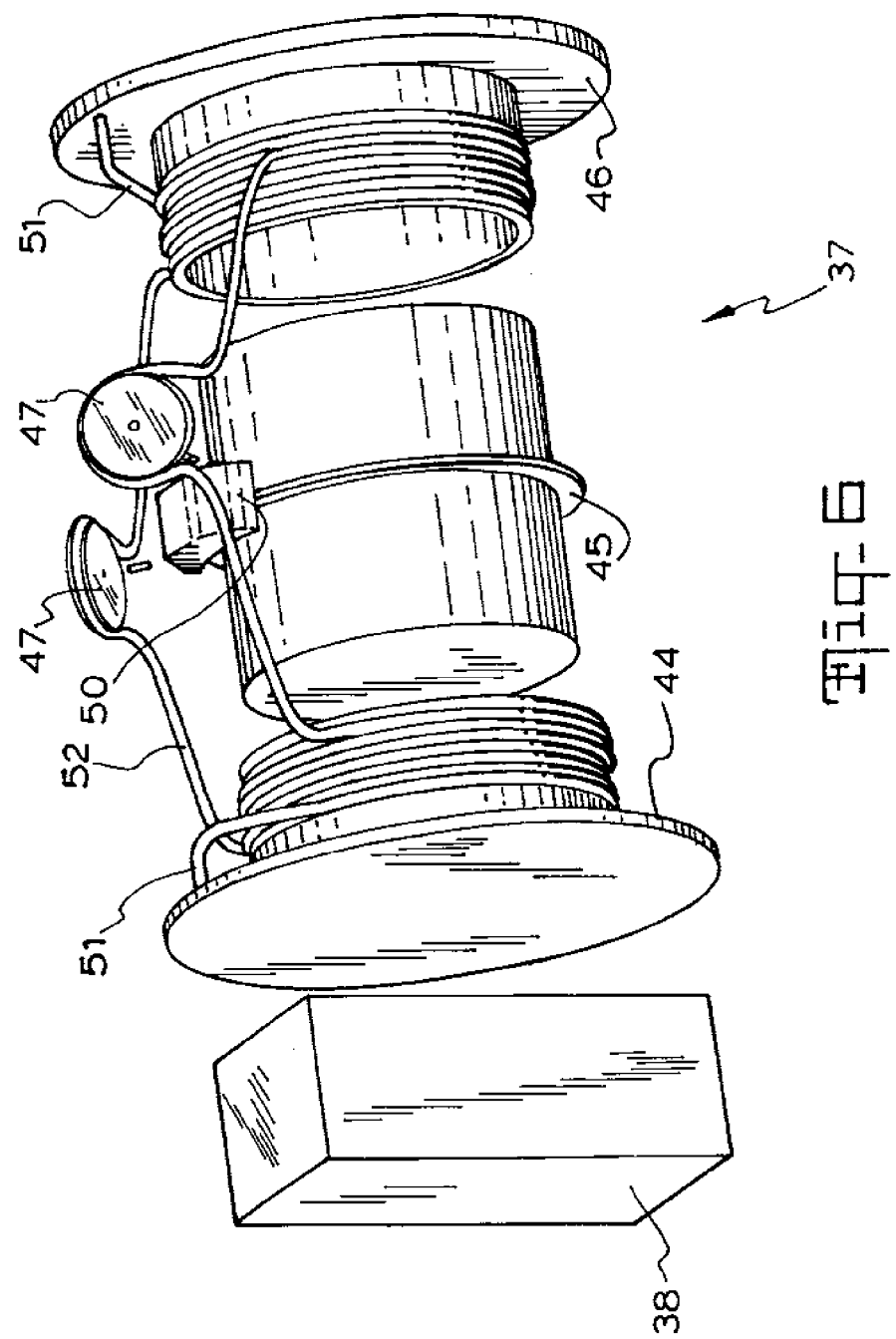
FIG. 6 is an exploded view of a cable spooler suitable for use in the rotating cuff of the tool head of FIG. 3.
Figures 7, 8:
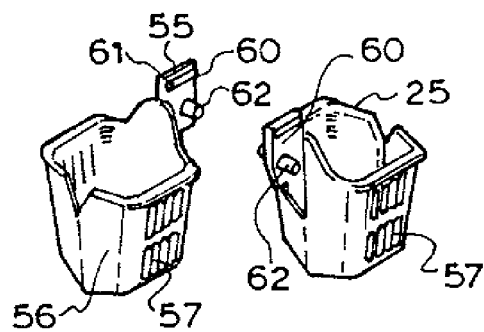
FIGS. 7 to 12 are front and rear perspective views respectively of medium, small and large plantlet holders for use in the present invention.
Figures 9, 10:
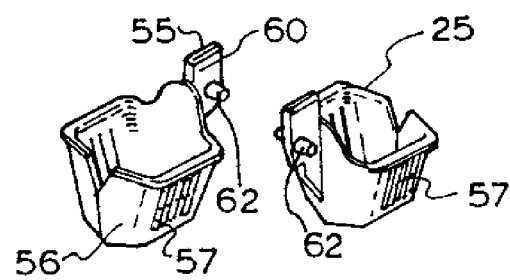
Figures 11, 12:
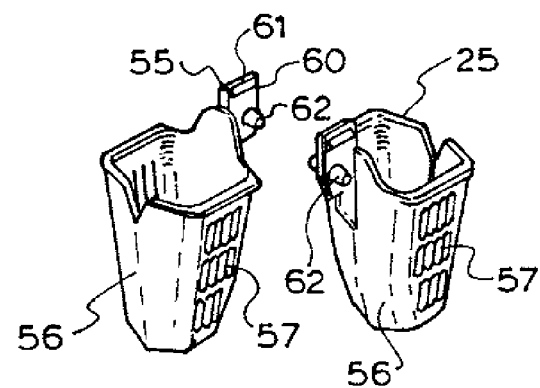

As illustrated in FIG. 3, the tool head 16 includes a rotating tool mount 36 rotatable relative to the robot arm 12 on a rotating cuff assembly 37, described in more detail in FIG. 6. The rotating tool mount 36 mounts a tool assembly 38 consisting of a pair of multipurpose gripper/closure assembly manipulator arms 40. The arms 40 each have a gripper end 41 and a closure manipulating end 42. The arms 40 are actuated by a common electromechanical actuator 43.

In FIG. 6, the rotating cuff assembly 37 is shown in an exploded and symbolic view, wherein the tool assembly 38 is fixed to a rotating spooler 44 which is spigoted for rotation on an intermediate idler carrier 45. The idler carrier 45 in turn is spigoted into a hollow bore of a fixed spooler 46 secured to the robot arm 12. The idler carrier 45 carries a pair of idler pulleys 47 on a pulley mount 50.

An electrical control cable 51 spools from the fixed spooler 46 to the rotating spooler 44 and back via an idler pulley 47 depending on the rotation of the tool assembly 38. A counter-tensioning cord 52 also spools from the rotating spooler 44 to the fixed spooler 46 and back via an idler pulley 47 depending on the rotation of the tool assembly 38. A drive shaft (not shown) passes from an actuator in the robot arm 12 axially though the fixed spooler 46 and the idler carrier 45 and rotates the tool assembly 38 as required by an operating program.

The net effect is that the tool assembly can be rotated through as many full rotations as there are rotations stored on the respective spoolers 44, 46, with the idler carrier 45 and idler pulleys 47 in assembly controlling the bight to prevent looping.

Figure 13:
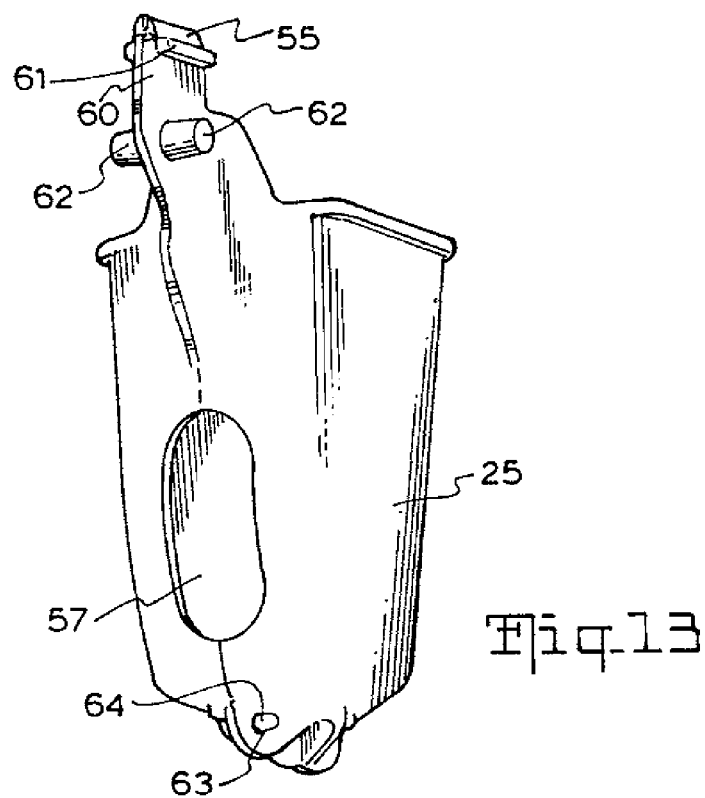
FIGS. 13 and 14 are front and rear perspective views of a plantlet holder for use in the present invention.
Figure 14:
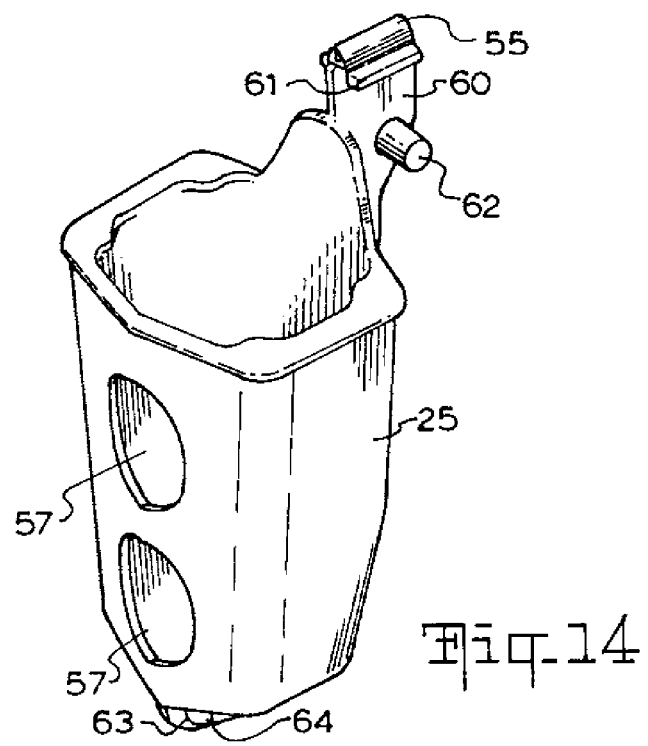
Figure 15:
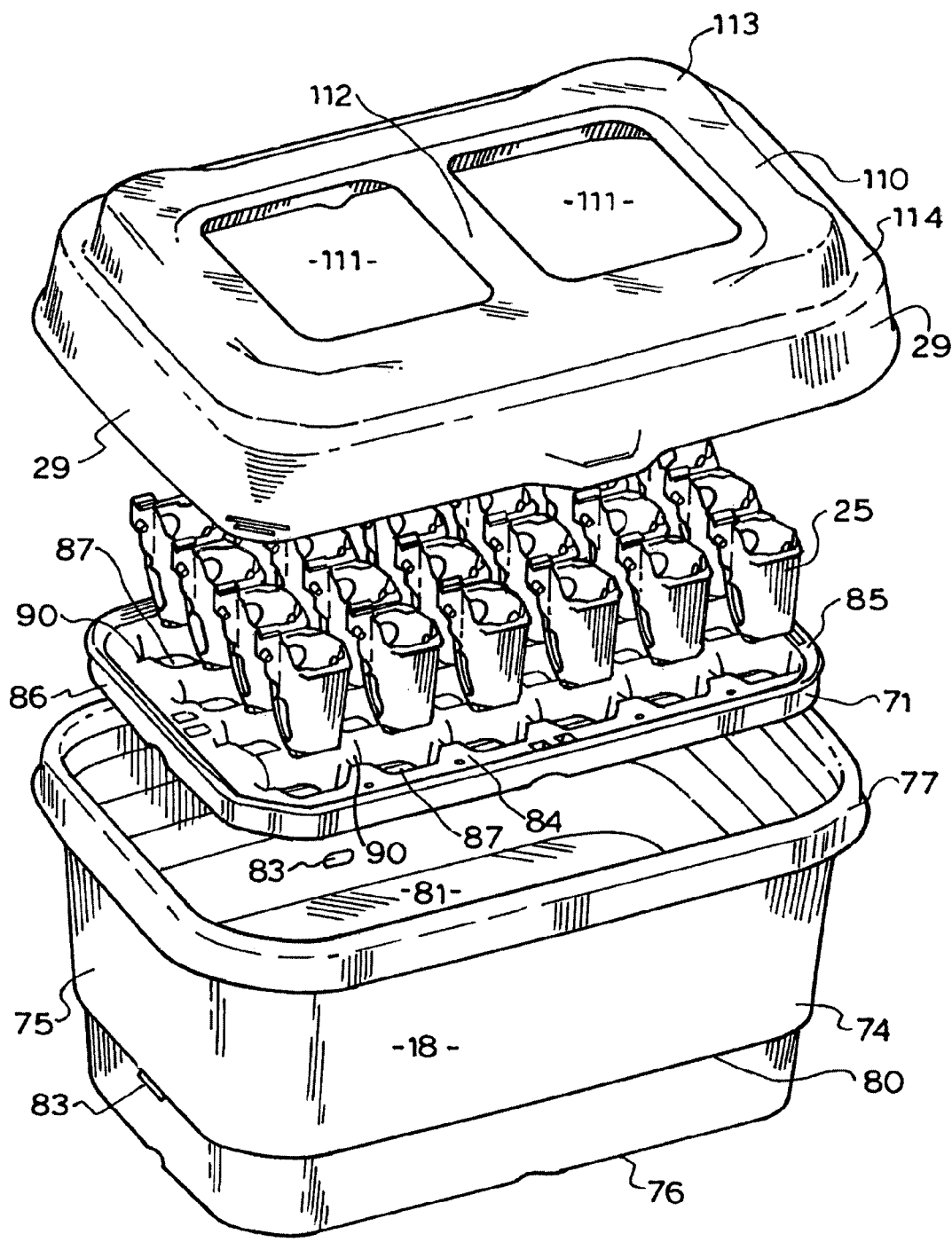
FIG. 15 is an exploded perspective view of a plantlet handling system in accordance with the present invention.

In the embodiment of FIGS. 7 to 15 there is provided a plantlet handling apparatus, wherein FIGS. 7 to 14 are variations on a plantlet holder 25 and FIG. 15 is of the apparatus in context, including a housing 18 formed of a light-transmitting polypropylene, a plantlet holder support 71 similarly moulded in polypropylene, a plurality of the plantlet holders 25, and a closure assembly 29.

In FIGS. 7 to 12, plantlet holders 25 are small, medium and large as indicated, but have in common that they are assembled in two conjoined halves about a vertical plane including a unitary self-hinge portion 55. The plantlet holders 25 present a plant holder portion 56 having root and nutrient apertures 57 and a handling portion 60 including gripper nibs 61 and pegs 62. The handling portion 60 and pegs 62 are adapted to engage the slot 30 and transverse groove 31 of the work stand 24.

In FIGS. 13 and 14, a plantlet holder 25 is produced by injection moulding a multiple strip. Excising from the strip leaves the two halved conjoined by the self-hinge 55 and indexing aperture 63 and pins 64.

The indexing apertures 63 enable the multiple plantlet holder strip to be positioned relative to a shearing device which accurately separates the plantlet holders 25 from the multiple strip, by shearing across a central spine through guide apertures. The plantlet holder 25 halves have a tapering form from the top to a base having respective pins 64 and holes 63 which retain the two plantlet holder halves together when the halves are closed together by bending about the self hinge crease 55.

The plantlet holder 25 when assembled has a pair of apertures 57 in one side disposed about the partition line, and a single large aperture 57 in the opposite side again disposed symmetrically about the partition line. The handling tab portions in the assembled plantlet holder 25 present single handling portions 60 having opposed respective handling pins 62 and handling nibs 61, and are adapted to be gripped by a handling robot. The handling portion doubles as a means for positive orientation by engaging in use in the slot 30 of the plantlet holder support 24.

In the assembly of a plant handling apparatus of FIG. 15, the housing 18 comprises side 74 and end 75 walls which are divergent up from a base wall 76 to provide for stack ability of the housings 18. The upper edges 77 of the side and end walls form a reinforced edge including a mechanical engagement for the closure assembly 29. There is provided a step 80 in the side 74 and end 75 walls and providing an annular supporting land 81 on the inside of the housing 18. The base wall 76 is formed with re-entrant portions 82 which enable the apparatus to be stacked complete with inserted holder supports 71 and plantlet holders 25 for shipping. The side walls 74 are provided with moulded nibs 83. The side ones of the nibs 83 may provide for positive engagement in position of the plantlet holder support 71 on the land 81. The end ones of the nibs 83 cooperate with the latching means 19.

The plantlet holder support 71 is unitarily moulded of polypropylene and has a body portion 84 bounded by a peripheral bead 85 disposed between the body portion 84 and a downward depending peripheral flange 86. In use the flange 86 supports the plantlet holder support 71 on the land 81 and the bead 85 clips under the nibs 83. The body portion 84 includes a plurality of apertures 87 in array on the body portion 84. The apertures 87 are shaped to accept the plantlet holders 72 and include a downward depending flange adapted to conform to an outer surface of the plantlet holder 72 and a recess portion 90 providing positive orientation of the plantlet holder 72, by means that will become apparent hereunder. The body portion 84 also includes indexing and handling apertures.

The closure assembly 73 comprises a polypropylene moulded body portion 110 having formed in the upper surface a pair of windows 111 formed in a raised portion 112 which provides some stiffening of the upper surface. The upper surface is bounded by a peripheral stiffening ridge 113 which forms the inner boundary of a mechanical engagement portion 114 adapted to sealingly engage the complementary upper edges 77 of the side and end walls.

The inner, downward-depending edge 115 forms a drip line inside the housing in use. An outer flange 116 extends down past the upper edge 77 in use to define a dead space 117 which resists convection mixing.

The windows 111 are closed off by a biaxially oriented polypropylene (BOPP) film heat sealed to the raised portion 112 in order to provide a closure assembly that is substantially sealed to the housing to reduce the risk of biological contamination while permitting exchange of metabolic gases.

In the example of FIG. 16, the drip line inside the housing in use is provided by a formed blade edge 120.

Apparatus in accordance with the foregoing embodiments are mechanical devices that support individual tissue culture plantlets, allowing them to be readily handled as individuals for transfers between tissue culture flasks, and transfer ex-vitro to soil or other growing medium. The plantlet holder provides a solid projection for mechanical gripping and movement of individual plantlets without touching the plantlet shoots or roots directly.

While illustrated with application of micro-propagation methods, the plantlet holder system is applicable to many types of plant tissue culture, including organogenesis or somatic embryogenesis, and to transformation/regeneration systems. The plantlet holder system can be used with manual methods of handling using forceps and similar gripping tools; the system is also suitable for machine controlled tools to facilitate mechanized handling methods.

The components of the robotic consumables facilitate positioning and handling features for rapid loading of the custom robotic platform and removal and storage of lids. All components have been designed for manufacturing and assembly efficiency, and will nest and stack in all assembly variations for volume efficiency in transport, sterilisation, media filling, and laboratory storage and tissue culture growth. Space efficiency is high with typical growing density (per layer) of 1000 plantlets/m$^2$.

The present plantlet holder system enables rapid and efficient robotic handling. Plantlets are conveniently presented to operators in an ergonomically appropriate way for easy dissection and transfer, with presentation interval of approximately six seconds. Operator efficiency is increased about five-fold over conventional tissue culture. These capabilities of the present system provide a powerful platform that radically changes the efficiency, capacity, quality and management of plant tissue culture operations. It is adaptable to different plant architectures, making it suitable for most, if not all, tissue culture systems. The flexible control of growth conditions may also make tissue culture successful with targets that are otherwise recalcitrant. More importantly, with the price sensitivity of many prospective targets, cost reductions possible from the present system can dramatically increase market demand.

It will of course be realised that while the above has been given by way of illustrative example of this invention, all such and other modifications and variations thereto as would be apparent to persons skilled in the art are deemed to fall within the broad scope and ambit of this invention as is set forth herein.

The invention claimed is:
1. Robotic plantlet handling apparatus including:
 a workstation having an operator work portion, a material source portion, a material delivery portion and a robot arm;

at least one housing located at the material source portion and containing a plurality of plantlet holders, the plantlet holders each comprising an open-topped container having apertures open to nutrient medium in use and having a handling lug, the housing being closable by a lid having a complementary engagement periphery adapted to mechanically and sealingly engage a corresponding peripheral lip of the housing;

at least one said housing located at said material delivery portion and adapted to receive a plurality of said plantlet holders;

a plantlet holder manipulator on said robot arm and adapted to engage said handling lug for movement of a plantlet holder between said material source portion, said operator work portion, and said material delivery portion; and a closure manipulator on said robot arm and selectively operable to engage a said lid for removal from and attachment to the housing.

2. Robotic plantlet handling apparatus according to claim 1, wherein the workstation is selected from a positive pressure, laminar flow and glove box workstation.

3. Robotic plantlet handling apparatus according to claim 1, wherein the operator work portion includes one or more work stands adapted to receive and retain a plantlet holder for a worker to operate on the plantlet in the holder.

4. Robotic plantlet handling apparatus according to claim 3, wherein the work stand includes a slot adapted to receive the handling lug of the plantlet holder.

5. Robotic plantlet handling apparatus according to claim 3, wherein the operator work portion comprises a hinged platform movable to permit changing out of a waste and reject holder located beneath an opening in the platform, said platform mounting the work stands.

6. Robotic plantlet handling apparatus according to claim 3, wherein the operator work portion includes a plurality of work stands each including operator prompt means adapted to cause the operator to time actions in concert with the robot arm.

7. Robotic plantlet handling apparatus according to claim 6, wherein the operator prompt means comprises one or more LED indicators operated by control means associated with the robot arm.

8. Robotic plantlet handling apparatus according to claim 3, wherein the work stand includes retaining means selectively operable to retain and release a plantlet holder.

9. Robotic plantlet handling apparatus according to claim 1, wherein the material source portion includes an array comprising a plurality of housings and including location means for the respective housings to assist the robot arm operation by location of the plantlet holders within tolerance of discrete positions.

10. Robotic plantlet handling apparatus according to claim 1, wherein the material source portion includes a lid locator to allow for storage of a respective lid removed from a housing and/or spare lids.

11. Robotic plantlet handling apparatus according to claim 1, wherein the material delivery portion includes an array comprising a plurality of housings and including location means for the respective housings to assist the robot arm operation by location of the plantlet holders within tolerance of discrete positions.

12. Robotic plantlet handling apparatus according to claim 1, wherein the material delivery portion may include a lid locator to allow for storage of a lid to be fitted to a housing and/or spare lids.

13. Robotic plantlet handling apparatus according to claim 1, wherein the robot arm comprises a multi-axis robot arm controlled by a robotic controller and terminating in the plantlet holder manipulator.

14. Robotic plantlet handling apparatus according to claim 1, wherein the plantlet holder manipulator comprises a gripper assembly having a pair of gripper ends adapted to engage the handling tab of the plantlet holder and selectively operable under robotic control by means selected from electromechanical and pneumatically operated actuators.

15. Robotic plantlet handling apparatus according to claim 1, wherein the closure manipulator on the robot arm comprises a pair of arms having outer ends adapted to engage engagement portions on the lid whereby relative movement of the respective outer arm ends toward each other causes an installed lid to be released by distortion from the housing, the outer arm ends being further adapted to retain the removed lid.

16. Robotic plantlet handling apparatus according to claim 1, wherein the closure manipulator shares a common actuator with the gripper assembly.

17. Robotic plantlet handling apparatus according to claim 16, wherein the closure manipulator is integrated with the gripper assembly forming the plantlet holder manipulator to form a gripper/closure manipulator assembly.

18. Robotic plantlet handling apparatus according to claim 17, wherein the gripper/closure manipulator comprises a manipulator body mounted on the robot arm, a pair of arms each having a gripper portion disposed at one end of the arm and a closure manipulator portion disposed at the other end of the arm, the arms each being pivoted to the manipulator body between the gripper portion and a closure manipulator portion to form a gripper and a closure manipulator, and actuator means mounted on the manipulator body to work the arms in concert to operate said gripper and closure manipulator.

19. Robotic plantlet handling apparatus according to claim 1, wherein the plantlet holder manipulator and closure manipulator are mounted on the robot arm on a rotatable cuff to enable selective deployment of the grippers and closure manipulator by rotation of the cuff.

20. Robotic plantlet handling apparatus according to claim 19, wherein actuators of the plantlet holder manipulator and closure manipulator are selected from pneumatic or electromechanical actuators, and the rotatable cuff includes means to control the spooling of control cables or tubes to enable rotations of more than +/−180°.

21. Robotic plantlet handling apparatus according to claim 20, wherein the rotatable cuff includes two or more relatively rotatable spoolers whereby a connecting cable to the actuators is wound from one spooler to the other and back as the plantlet holder manipulator and closure manipulator are rotated in assembly.

22. Robotic plantlet handling apparatus according to claim 21, wherein the respective spoolers are separated by a half-speed idler carrier having low-friction leads or rollers for the laying or playing out of the cables or tubes on or from the respective spoolers.

23. Robotic plantlet handling apparatus according to claim 1, wherein the housing includes integrally formed sealing means adapted to cooperate with the lid to provide the substantially airtight seal.

24. Robotic plantlet handling apparatus according to claim 1, wherein the material source portion and material delivery portion each include location means comprising a housing holder.

25. Robotic plantlet handling apparatus according to claim 24, wherein the housing holder is a plate having apertures for accepting a plurality of housings.

26. Robotic plantlet handling apparatus according to claim 25, wherein the plate includes latching means to provide selectively releasable, positive retention of the housing in the housing holder, the housing being formed with nibs formed in a side wall to cooperate with the latching means.

27. Robotic plantlet handling apparatus according to claim 1, wherein the lid comprises a peripheral flange that extends downward and external of the housing lip to define an annular dead space that is not subject to convection mixing with the environment.

28. Robotic plantlet handling apparatus according to claim 27, wherein the peripheral flange extends below a sealing rim of the housing by at least 3 mm.

29. Robotic plantlet handling apparatus according to claim 1, wherein the lid has an inner peripheral flange that is spaced inwardly of and extends downward of a housing lip to define an annular drip line for condensation away from the lip.

30. Robotic plantlet handling apparatus according to claim 1, wherein the lid has a gas permeable portion formed of a material selected from film material and fibrous material selected to allow exchange of metabolic gases produced or required by plantlets.

31. Robotic plantlet handling apparatus according to claim 30, wherein the material is selected from hydrophobic polyolefin materials.

32. Robotic plantlet handling apparatus according to claim 1, wherein the plantlet holders have a side wall relieved downward of an upper edge to provide access for a scalpel to trim or excise new plantlets from a plant in the holder.

33. Robotic plantlet handling apparatus according to claim 1, wherein the handling lug comprises a cross pin or laterally extending pair of pegs, wherein the handling lug engagement portion of the work stand comprises a pillar mounted to the work station and having a bifurcated top admitting a portion of the handling lug and a an upper transverse groove extending either side of the bifurcation of the top and adapted to receive the cross pin or pegs.

34. Robotic plantlet handling apparatus according to claim 1, wherein the robot arm comprises computer controlled mechanical handling means including a robotic controller.

35. A plant cloning method including the steps of:
(i) providing a workstation having an operator work portion, a material source portion, a material delivery portion and a robot arm;
(ii) locating in said workstation at least one housing at the material source portion and containing plantlets in a plurality of plantlet holders, the plantlet holders each comprising an open-topped container having apertures open to nutrient medium in use and having a handling lug, the housing being closed by a lid having a complementary engagement periphery adapted to mechanically and sealingly engage a corresponding peripheral lip of the housing;
(iii) locating in said workstation at least one housing at said material delivery portion and adapted to receive a plurality of said plantlet holders;
(iv) operating said robot arm and a closure manipulator thereon to engage and remove said lid and deliver the lid to a storage location;
(v) operating said robot arm and a plantlet holder manipulator thereon to engage the handling lug of and remove a plantlet holder from the housing at the material source portion and deliver the holder to a work stand adapted to receive and retain the plantlet holder for a worker to operate on the plantlet in the holder;
(vi) operating on the plant material to produce one or more product-containing plantlet holders;
(vii) operating said robot arm and a plantlet holder manipulator thereon to engage the handling lug of and remove a plantlet holder from a work stand to a said housing at said material delivery portion;
(viii) repeating step (vii) to exhaust product bearing plantlet holders on work stands;
(ix) repeating steps (v) to (viii) until a said housing at said material delivery portion is loaded; and
(x) operating said robot arm and said closure manipulator thereon to engage a lid and install the lid on said loaded housing.

* * * * *